(12) United States Patent
Pyo et al.

(10) Patent No.: US 8,163,940 B2
(45) Date of Patent: Apr. 24, 2012

(54) METHOD FOR PREPARATION OF AMORPHOUS, ANHYDROUS CRYSTALLINE OR HYDRATED CRYSTALLINE DOCETAXEL

(75) Inventors: Sang-Hyun Pyo, Chungcheongnam-do (KR); Jin-Suk Cho, Daejeon (KR); Moon-Suk Kim, Busan (KR); Bong-Kyu Song, Daejeon (KR); Ho-Joon Choi, Daejeon (KR)

(73) Assignee: Samyang Genex Corporation, Seoul (KR)

( * ) Notice: Subject to any disclaimer, the term of this patent is extended or adjusted under 35 U.S.C. 154(b) by 823 days.

(21) Appl. No.: 12/159,812

(22) PCT Filed: Nov. 2, 2006

(86) PCT No.: PCT/KR2006/004539
§ 371 (c)(1),
(2), (4) Date: Jul. 29, 2008

(87) PCT Pub. No.: WO2007/078050
PCT Pub. Date: Jul. 12, 2007

(65) Prior Publication Data
US 2009/0018353 A1  Jan. 15, 2009

(30) Foreign Application Priority Data
Jan. 2, 2006 (KR) .................. 10-2006-0000276

(51) Int. Cl.
*C07D 305/00* (2006.01)
*C07D 407/00* (2006.01)
(52) U.S. Cl. ........................ 549/510; 549/511
(58) Field of Classification Search .............. 549/511, 549/510
See application file for complete search history.

(56) References Cited

U.S. PATENT DOCUMENTS

| 6,838,569 B2 | 1/2005 | Sharma et al. |
| 6,881,852 B2 * | 4/2005 | Sharma et al. ............ 549/510 |

FOREIGN PATENT DOCUMENTS

| EP | 1 623 982 A1 | 2/2006 |
| KR | 10-2000-0042499 A | 7/2000 |
| KR | 10-0391753 | 7/2003 |
| WO | WO2004/099167 | 4/2004 |
| WO | WO-2005/061474 | 7/2005 |
| WO | WO-2007/044950 | 4/2007 |

OTHER PUBLICATIONS

International Search Report and Written Opinion. PCT/KR2006/04539 mailed Oct. 29, 2007, 5 pages.
Hancock et al. What is the True Solubility Advantage for Amorphous Pharmaceuticals?, Sep. 20, 1999, pp. 397-404.
Lee et al., Preparation and Characterization of Solvent Induced Dihydrated, Anhydrous, and Amorphous Paclitaxel, 2001, vol. 22, No. 8, pp. 925-928.
European Search Report dated Oct. 14, 2010. EP 06 812 378.5.

* cited by examiner

*Primary Examiner* — Andrew D Kosar
*Assistant Examiner* — Raymond Covington
(74) *Attorney, Agent, or Firm* — Gifford, Krass, Sprinkle, Anderson & Citkowski, P.C.

(57) ABSTRACT

This invention is directed to a method for the preparation of docetaxel having an amorphous, anhydrous crystalline, or hydrated crystalline structure. In accordance with the invention, highly pure amorphous, anhydrous crystalline, or hydrated crystalline docetaxel can be produced with a high yield by using a solvent precipitation method, colloid formation method, etc.

3 Claims, 9 Drawing Sheets

METHOD FOR PREPARATION OF AMORPHOUS, ANHYDROUS CRYSTALLINE OR HYDRATED CRYSTALLINE DOCETAXEL

CROSS-REFERENCE TO RELATED APPLICATIONS

This application is the U.S. national phase of PCT/KR2006/004539 filed Nov. 2, 2006, which claims priority to and the benefit of Korean Patent Application No. 2006-0000276 filed on Jan. 2, 2006, which is hereby incorporated by reference for all purposes as if fully set forth herein.

BACKGROUND OF THE INVENTION (a) Field of the Invention

The present invention relates to a method for obtaining highly pure amorphous, anhydrous crystalline, or hydrated crystalline docetaxel with a high conversion rate and a high yield by solvent precipitation, colloid formation, etc., using several solvents.

(b) Description of the Related Art

Docetaxel has been used as one of the important anticancer agents together with paclitaxel. Docetaxel is semi-synthesized by obtaining its precursors such as 10-deacetylbaccatin III, baccatin III, etc., from the leaves and stems of yew and converting them into docetaxel by chemical reactions.

Like paclitaxel, docetaxel shows very low solubility in most pharmaceutical solvents including water, and accordingly there are numerous restrictions on its formulation and prescription.

The solubility of a material is influenced by its solid-state properties, and it has been suggested that the solubility of an amorphous structure is 10 times to 1600 times higher than that of its most stable crystalline structures (Bruno C. Hancock and Michael Parks, What is the true solubility advantage for amorphous pharmaceuticals. Pharmaceutical Res. 2000, 17, 397-404). This indicates that while solubility against a specific solvent is largely determined by the properties of the materials themselves, it can be improved by altering the configuration of the materials. Besides the change in the configuration of materials, solubility and dissolution rate can be improved by making the particle size of the materials small, thereby enlarging their surface area. On the other hand, in the case that the configuration of particles is amorphous, in general, their stability is decreased over storage time when compared with crystalline structures. Korean Patent No. 10-0391753 by Jacques Doveze, et al. discloses that docetaxel hydrate is more stable than its anhydrate.

Accordingly, as the properties of docetaxel vary by its final morphologies including amorphous form, crystalline form, hydrate, and anhydrate, there is a need to selectively obtain it having a suitable morphology according to its intended use. So far, however, there have been few known methods of selectively obtaining docetaxel having a specific morphology.

Recently, due to the stability of hydrates, there has been increasing interest in methods for the preparation of docetaxel hydrate. Jacques Doveze, et al., describes in Korean Patent No. 10-0391753 that docetaxel trihydrate is obtained by crystallizing docetaxel from a mixture of water and aliphatic alcohol having 1 to 3 carbon atoms and drying the obtained products at a temperature of about 40° C. and a reduced pressure of 4 to 7 kPa, in a humid atmosphere where the relative humidity is controlled to about 80%. The method proposed therein comprises crystallization and hydration steps. In the crystallization step, docetaxel is dissolved in aliphatic alcohols having 1 to 3 carbon atoms preferably at temperatures of 40 to 60° C., to which purified water is then added at the same temperature and then cooled to produce crystals. In the embodiment, it is described that 303 g of docetaxel was heated to 50° C. until it was completely dissolved in 0.983 L of ethanol, and while the temperature of 50° C. was being maintained, 4.39 L of purified water was added thereto over 1 hour. Such a crystallization process, however, requires heating for at least 1 hour up to high temperatures under the solvents and there arises the problem that docetaxel may be degraded due to its instability. Although it showed that the titer of the specimen used in the embodiment was improved to 98.7% from its initial 92.4% through crystallization, the degraded matter from the crystallization process may be included in the included impurities. Therefore, it would have been advisable for the described embodiment to evaluate and compare the impurities occurring during the processes using docetaxel with a high purity of as high as 99.5% because it was the final step of the manufacturing processes for determining the morphology of the final products. Thus, there is a limit in that it ignored evaluation of degradation products that could be generated during the crystallization process by using a specimen having low titer.

Arun Prakash Sharma, et al., disclose in U.S. Pat. No. 6,838,569 a process for the purification of paclitaxel and docetaxel trihydrates. In the above process, partially purified docetaxel is purified under the conditions of alkane-chloroalkane, acetone-hexane into a chromatography purity of 99.53%, which is then crystallized using acetonitrile and water. After the purified docetaxel is dissolved in acetonitrile at 50 to 70° C., to which purified water is slowly added, it is subjected to additional agitation at 15 to 20° C., to thereby obtain precipitates. The process disclosed in the above patent, although it did not mention dissolution time, cannot avoid the degradation of docetaxel by warming it to 50 to 70° C. even though there was little change in purity before and after crystallization. Moreover, as the applied process is the final purification step, recovery rate can be a very essential factor. The embodiment of this patent showed that 415 g of trihydrate (moisture 6.8%) was obtained from 460 g of anhydrate prior to crystallization, but in consideration of moisture, actual yield corresponds to approximately 84% which is considered to be comparatively low. This is one of the drawbacks that can be seen in common re-crystallization.

Li Jinliang, et al., discloses in International Patent Publication WO2004/099167 a method for the preparation of trihydrate by crystallizing anhydrous docetaxel in a mixed solution of purified water and acetone. In the embodiment, 87 g of anhydrate was dissolved in acetone, to which purified water at 1.5 times thereof was then added, and it was then crystallized at 0° C. for two days to thereby prepare 85 g of trihydrate (moisture 6.43%). However, this method is also a common re-crystallization method, and actual recovery rate is as low as 91% in consideration of moisture amount.

Lee, et al., proposed a method for the preparation of amorphous, anhydrous crystalline, or hydrated crystalline paclitaxel using several solvents (Jeong Hoon Lee, Un-Sook Gi, Jin-Hyun Kim, Yongae Kim, Seon-Ho Kim, Hunseung Oh, and Bumchan Min, Preparation and characterization of solvent induced dihydrated, anhydrous, and amorphous paclitaxel, Bull. Korean Chem. Soc., 2001, 22, 925-928). In this method, the crystalline structure of paclitaxel can be selected by the several applied solvents, but reduced pressure drying and re-crystallization pose numerous problems as follows.

First, in the case of simple reduced pressure drying by Lee, et al., as paclitaxel is dried while being gelled as if it is coated onto a container that is used during the drying process, recovery is very difficult. Also, as the size of particles to be formed is very large, they are still very large at above 100 μm even after recovery and fragmentation. Such a big particle size can be a cause of solubility decrease and make drying difficult while keeping the amount of remaining solvents in an infinitesimal quantity. In medical products used for medical purposes, each solvent should remain below a certain level according to ICH guidelines (International Conference on Harmonisation of Technical Requirements for Registration of Pharmaceuticals for Human Use), and in the case of drying by methods such as reduced pressure evaporation, it takes considerable time to sufficiently lower the level of remaining solvents because of particle size and the properties of the particles. Further, existing re-crystallization methods have a low yield due to the very nature of the process, they are required to be carried out for a long time at a low temperature, and the size of crystals to be formed is large.

SUMMARY OF THE INVENTION

In order to solve the aforementioned problems, it is an object of the present invention to provide a method of efficiently and selectively preparing docetaxel having amorphous, anhydrous crystalline, or hydrated crystalline form using several solvents.

BRIEF DESCRIPTION OF THE DRAWINGS

FIGS. 1A and 1B show HPLC analysis results using HPLC showing change in the purity of docetaxel before and after the preparation process of Example 1, wherein

FIG. 7A to 7C show HPLC and XRPD analysis results showing purity change before and after a preparation process with regard to docetaxel prepared by agitation at room temperature after solvent precipitation at a high temperature of Comparative Example 1, wherein FIG. 7C shows XRPD analysis results.

DETAILED DESCRIPTION OF THE PREFERRED EMBODIMENTS

A more complete appreciation of the invention, and many of the attendant advantages thereof, will be readily apparent as the same becomes better understood by reference to the following detailed description.

The present invention is directed to a method for the preparation of docetaxel including preparing amorphous, anhydrous crystalline, or hydrated crystalline docetaxel by solvent precipitation, colloid formation, etc., and obtaining it with a high conversion rate and a high yield.

The method for the preparation of docetaxel of the invention has the merit that it can efficiently produce docetaxel of fine particles with a high yield. Also, it enables docetaxel having a desired morphology to be obtained with a high conversion rate and a high yield by a simple method from the highly pure docetaxel while maintaining its purity.

All the preparation methods of docetaxel of the invention that follow are applicable to docetaxel-containing matter containing taxane substances other than docetaxel, as well as docetaxel as a single substance. The "docetaxel-containing matter" in the invention refers to substances containing taxane substances including paclitaxel together with docetaxel, wherein the amount (purity) of docetaxel is 50% or more, preferably 70% or more, more preferably 90% or more, and most preferably 98.5% or more.

First, the present invention provides a method of preparing amorphous docetaxel using solvent precipitation by polar-nonpolar solvents. While docetaxel is sparingly soluble as described in the above, it has been known that solubility of its amorphous structure is 10 times to 1600 times higher than that of a stable crystalline structure. In the prior arts, complicated and complex processes had to be carried out to obtain amorphous docetaxel, but this invention enables the preparation of amorphous docetaxel with a high conversion rate and a high yield in a simple and easy way by performing solvent precipitation using specific polar-nonpolar solvents.

The method for the preparation of amorphous docetaxel of the invention comprises the following steps:

dissolving docetaxel-containing matter or docetaxel in a polar solvent;

adding the above-obtained solution to a nonpolar solvent to produce precipitates; and filtrating and drying the produced precipitates to obtain amorphous docetaxel.

In the above method for the preparation of the amorphous docetaxel, the polar solvent is preferably selected from the group consisting of halogenated alkanes, ketones, and mixed solvents thereof. As the halogenated alkanes, dichloromethane, chloroform, and the like can be used, and the ketones can be acetone. It is advisable that the docetaxel is dissolved in the polar solvent at a concentration of 1 to 30% (w/v), preferably 5 to 20% (w/v) for initial purity maintenance and a high yield of highly pure amorphous docetaxel.

For the above nonpolar solvent, it is preferable to use at least one solvent selected from the group consisting of alkanes, cycloalkanes, and nonpolar solvents having polarity values of not more than that of diisopropylether because instant precipitation can occur. The alkanes are hexane or pentane, the cycloalkanes are cyclohexane or cyclopentane, and the nonpolar solvents having polarity values of not more than that of diisopropylether can be dialkylether.

In the step of adding the solution where the docetaxel-containing matter or docetaxel is dissolved in the polar solvent to the nonpolar solvent, the volume of the nonpolar solvent is preferably 5 times or higher than that of the volume of the solution to be added, and more preferably, the volume ratio of the solvent and the nonpolar solvent is 1:8 to 1:20. If the amount of the nonpolar solvent used deviates from the above ranges, it is difficult to cause efficient precipitation. The thus-obtained precipitates are filtrated under a reduced pressure and dried whereby amorphous docetaxel can be obtained in an easy and simple way.

Also, the invention provides a method of preparing anhydrous crystalline docetaxel by colloidizing a docetaxel-containing matter or docetaxel in a colloid-formable solvent in a suspended state and then drying it under a reduced pressure. While the anhydrous crystalline docetaxel has excellent storage stability, it shows low solubility. However, according to the inventive preparation method, as the particles of docetaxel to be obtained are very fine, its solubility can be remarkably improved. Accordingly, the invention is to provide a method for the preparation of anhydrous crystalline docetaxel having improved solubility as well as excellent storage stability.

The method for the preparation of anhydrous crystalline docetaxel of the invention comprises the following steps:

colloidizing a docetaxel-containing matter or docetaxel in a colloid-formable solvent in a suspended state, not being completely dissolved; and evaporating the solvent among the obtained colloid solution and drying it under a reduced pressure to obtain anhydrous crystalline docetaxel of fine powders.

The above colloid-formable solvent for docetaxel does not completely dissolve docetaxel but renders it able to remain in a suspended state, and acetone can be used.

When docetaxel is dissolved in acetone, docetaxel is added at a concentration of 1 to 30% (w/v), preferably 5 to 10% (w/v). The solvent evaporation can be carried out using a common Rotary evaporator and the temperature is preferably 35° C. to 40° C. In the context of the invention, "colloid" refers to a state where docetaxel is being suspended in a solvent, not being dissolved.

The preparation of anhydrous crystalline docetaxel by the above method has the merit that it can keep the level of remaining solvents low because the formation of fine particles is induced through the colloid and thus drying is easy, unlike the drawback of common reduced pressure dry methods as seen in the method of Lee, i.e., that particles grow as they are coated onto a container. Also, as the particle size of docetaxel to be obtained is as fine as 5 to 30 µm, solubility can be remarkably improved.

Also, the invention provides a method of preparing hydrated crystalline docetaxel by dissolving a docetaxel-containing matter or docetaxel in an organic solvent and precipitating it by addition of a purified water or buffer solution. A hydrated crystalline form is an advantageous morphology in respect of solubility, but the previous preparation methods of hydrated crystalline docetaxel decreases the stability of docetaxel because they are carried out at a relatively high temperature and they fail to keep initial purity of final products. However, the inventive method for the preparation of hydrated crystalline docetaxel is carried out at a relatively low temperature, and accordingly it is advantageous for the stability of docetaxel and it can keep the initial purity.

The method for the preparation of hydrated crystalline docetaxel includes the following steps:

dissolving a docetaxel-containing matter or docetaxel in an organic solvent at room temperature;

adding purified water or a buffer solution to the obtained solution;

allowing it to stand at −20° C. to 20° C., preferably 0° C. to 10° C., for 1 hour to 48 hours, preferably 5 hours to 24 hours, to produce a precipitate; and filtrating the produced precipitate to obtain hydrated crystalline docetaxel.

In the above method for the preparation of hydrated crystalline docetaxel, as the organic solvent, there can be used at least one selected from the group consisting of alcohols having 1 to 3 carbon atoms, e.g., methanol, ethanol, or propanol, and ketones, e.g., acetone and acetonitrile. The docetaxel is dissolved in the organic solvent at a concentration of 1 to 30% (w/v), preferably 5 to 20% (w/v).

The hydrated docetaxel obtained by the above method is not limited to a specific hydrated form, and it can be in the form of monohydrate, bihydrate, or trihydrate.

It is preferred that the purified water or buffer solution is added in a volume ratio of 10:4 to 10:15 (solution volume: purified water or buffer solution volume), preferably 10:10 to 10:12 (solution volume:purified water or buffer solution volume). When the volume ratio of the purified water is less than the above ranges, precipitation may be slow or no precipitate formation may occur. When the volume ratio of the purified water is higher than the above ranges, the volume of the solution may excessively enlarge during reaction, or the buffer solution, a phosphate buffer, or an ammonia buffer can be used.

The above method of obtaining hydrated crystalline docetaxel by dissolving a docetaxel-containing matter or docetaxel in an organic solvent at room temperature and precipitating it by addition of purified water employs a solvent similar to that proposed in Korean Patent No. 10-0391753 by Jacques Doveze, et al., but it has the merit of applicability to industrial fields in a very easy way.

That is, the method by Jacques Doveze is to dissolve an aliphatic alcohol having 1 to 3 carbon atoms at a temperature of 40 to 60° C., and it may cause a severe problem in terms of stability of docetaxel during the process. Although Jacques Doveze described that the purity of docetaxel that was obtained by dissolving it in alcohols at 50° C. for 1 hour and then forming crystals by the addition of purified water increased from 92.4% to 98.7%, the inventors found that when docetaxel having 99.7% purity was dissolved in methanol at 50° C. according to the same method in parallel with the performance of the present invention and then allowed it to stand from 0 hours to 24 hours, the purity was suddenly decreased from the purity analysis for 0 hour, 1 hour, 5 hours, 10 hours, and 24 hours, unlike Korean Patent No. 10-0391753 (see Comparative Example 2 below). When docetaxel was dissolved in methanol and maintained at 50° C. for at least 1 hour to complete reaction as described by Jacques Doveze, it was verified that the purity of docetaxel was decreased to 95.7% and docetaxel showed degradation. This result supports the general fact that docetaxel is degraded when it is warmed after dissolution in solvents such as alcohols. Thus, although the method by Jacques Doveze succeeded in the production of hydrated crystalline form, its manufacturing with high purity while securing the stability of docetaxel is difficult. In this respect, the solvent precipitation at a low temperature after dissolution at room temperature proposed in the present invention is very useful and applicable to industrial fields, being distinguishable from the above method. That is, while the method by Jacques Doveze attempted to raise yield by increasing the concentration of docetaxel in a solution, the inventive method for the preparation of hydrated crystalline docetaxel is characterized by determining the most suitable temperature ranges for the maintenance of high purity and stability of docetaxel in the knowledge that in the maintenance of high purity and stability of docetaxel, maintaining a temperature is a very essential factor.

Also, the invention provides, as another method for the preparation of hydrated crystalline docetaxel, a method of obtaining hydrated crystalline docetaxel by dissolving a docetaxel-containing matter or docetaxel in a mixed solvent of an organic solvent and purified water or a mixed solvent of an organic solvent and buffer solution and then causing precipitation by the concentration of the obtained solution at a reduced pressure.

The above method for the preparation of hydrated crystalline docetaxel using the mixed solvents includes the following steps:

dissolving a docetaxel-containing matter of docetaxel in a mixed solvent of an organic solvent and purified water or a mixed solvent of an organic solvent and buffer solution;

producing precipitates by evaporating the obtained solution, thereby eliminating the organic solvent among the mixed solvent; and filtrating the obtained precipitates at a reduced pressure and drying them to prepare hydrated crystalline docetaxel.

The hydrated docetaxel obtained by the above method is not limited to a specific hydrated form, and preferably, it can be in the form of monohydrate, bihydrate, or trihydrate.

For the organic solvent, there can be used at least one selected from the group consisting of alcohols having 1 to 3 carbon atoms, e.g., methanol, acetone, and acetonitrile, as a solvent that is well mixed with purified water. The organic solvent is used as a mixed solvent in mixture with the purified water or buffer solution, and it is advisable that the mixing ratio of the organic solvent and the purified water or buffer solution is 7:0.5 to 7:5, preferably 7:1 to 7:4 by volume. When the ratio of the purified water is lower than the above, precipitate formation may not occur well, and if it is higher than the above ratio, the volume of the reaction solution becomes too much. As the buffer solution, a phosphate buffer, an ammonia buffer, and the like can be used. The docetaxel is dissolved in the mixed solvent at a concentration of 0.1 to 5% (w/v), preferably 1 to 2% (w/v).

It is preferred that the evaporation is carried out at 35° C. to 40° C. water bath using a common Rotary evaporator.

The above method of obtaining hydrated crystalline docetaxel by dissolving a docetaxel-containing matter or docetaxel in a mixed solvent of an organic solvent and purified water or buffer solution, evaporating the solvent using a common Rotary evaporator, and filtrating and drying the formed precipitates enables the efficient production of docetaxel with a high yield within a short time. That is, as reduced pressure concentration proceeds after the dissolution of docetaxel in the mixed solvent of the organic solvent and purified water, the ratio of the remaining purified water or buffer solution increases because the organic solvent is evaporated faster than the purified water or buffer solution. Hence, as the solubility of docetaxel becomes low, precipitates begin to form. When the organic solvent is all evaporated, most of the docetaxel forms precipitates because the solubility of docetaxel against purified water is very low. If the formed precipitates are filtrated at a reduced pressure, a hydrated crystalline form can be relatively easily obtained and the obtained precipitates are characterized in that their particles are very small and the recovery rate is very high in comparison with crystallization methods. Furthermore, a hydrated crystalline form can be obtained by a stable method within a very short time in comparison with the crystallization methods.

Also, the invention provides, as still another method for the preparation of hydrated crystalline docetaxel, a method of preparing hydrated crystalline docetaxel by dissolving a docetaxel-containing matter or docetaxel in an organic solvent and causing precipitation by the addition of a quantity of purified water.

The above method for preparing hydrated crystalline docetaxel by dissolving docetaxel in an organic solvent and causing precipitation by the addition of a quantity of purified water comprises the following steps:

dissolving a docetaxel-containing matter or docetaxel in an organic solvent or a mixed solvent of an organic solvent and purified water at room temperature;

suspending and precipitating the obtained solution by slowly adding it to a quantity of purified water or buffer solution; and filtrating the obtained precipitate at a reduced pressure and drying it to obtain hydrated crystalline docetaxel.

The hydrated crystalline docetaxel obtained by the above method is not limited to a specific hydrated form, and it can be in the form of monohydrate, bihydrate, or trihydrate.

For the organic solvent, there can be used at least one organic solvent selected from the group consisting of alcohols having 1 to 3 carbon atoms, e.g., methanol that is mixed well with purified water, acetone, acetonitrile, and tetrahydrofuran. The organic solvent can be used alone, or it can be used as a mixed solvent in mixture of purified water. In the case that the organic solvent is used as a mixed solvent in a mixture of purified water, it is advisable that the concentration of the mixed solvent is 0.5% to 50% (v/v), preferably 10% to 30% (v/v).

The precipitate is obtained by slowly adding the above solution to the purified water or buffer solution at 1 to 20 times thereof, preferably 5 to 10 times thereof by volume.

The above method of obtaining hydrated crystalline docetaxel by dissolving docetaxel in an organic solvent and forming a precipitate by the addition of a quantity of purified water enables the stable production of a hydrated crystalline form within a very short time in comparison with current crystallization methods. Thus, if docetaxel is slowly added to a quantity of purified water after dissolution in the organic solvent or the mixed solvent of the organic solvent and purified water, as the solubility of docetaxel against purified water decreases, it is suspended and forms precipitates. Since the dissolution of docetaxel is carried out at room temperature and the formed precipitates can be obtained simply by a reduced pressure filtration method, the stability of docetaxel can be secured with a high recovery rate, and further, processing time is short and recovery is possible in a very easy way.

The present invention is further explained in more detail with reference to the following examples. These examples, however, should not be interpreted as limiting the scope of the present invention in any manner.

After docetaxel obtained by the methods described in the following examples were subjected to vacuum drying, their arrangement and particle size were verified through purity, yield, X-ray analysis (XRPD), and SEM (JSM-6635F, Jeol) X-ray analysis (XRPD), and purity analysis conditions are as seen in Table 1 and Table 2 below.

TABLE 1

| | |
|---|---|
| Measuring Machine | Rigaku, D/MAX 3B, XRPD |
| Measuring Methods | About 20 mg of specimen is fixed on XRPD sampler, and it is then scanned from 5° C. to 25° C. for minutes. |
| X-ray source | CuKα 40 kV, 40 mA |

The purity and recovery rate of docetaxel in the present specification were calculated by quantity analysis using HPLC under the conditions of Table 2.

TABLE 2

| | |
|---|---|
| Apparatus | Hewlett Packard 1100 HPLC |
| Column | Curosil PFP 4.6 × 50, 5 micron |

TABLE 2-continued

| | |
|---|---|
| Column Temperature | 35° C. |
| Mobile Phase | Acetonitrile:Water (35-65% concentration gradient) |
| Flow Rate | 1 ml/min |
| Injection Amount | 10 ul |
| Detector | UV(227 nm) |

EXAMPLE 1

Preparation of Amorphous Docetaxel 1

Figure 1A:
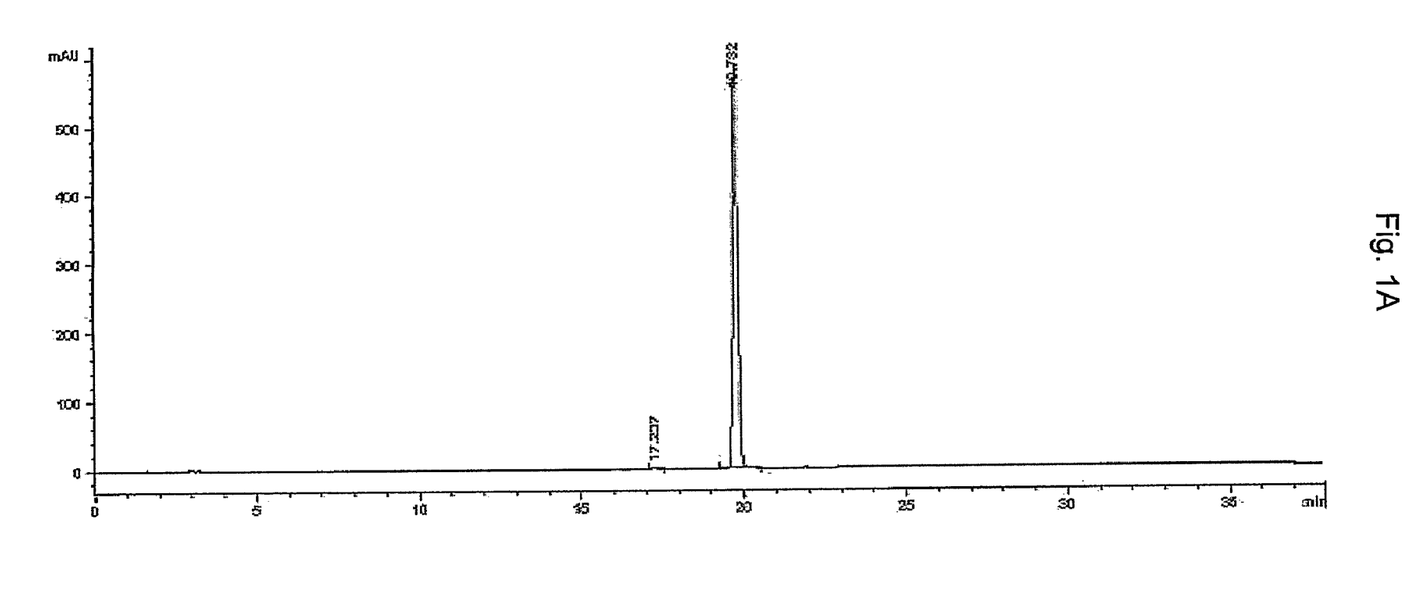
FIG. 1A shows HPLC analysis results of a specimen before the preparation process and FIG. 1B shows HPLC analysis results of the specimen after the preparation process was performed.
Figure 1B:
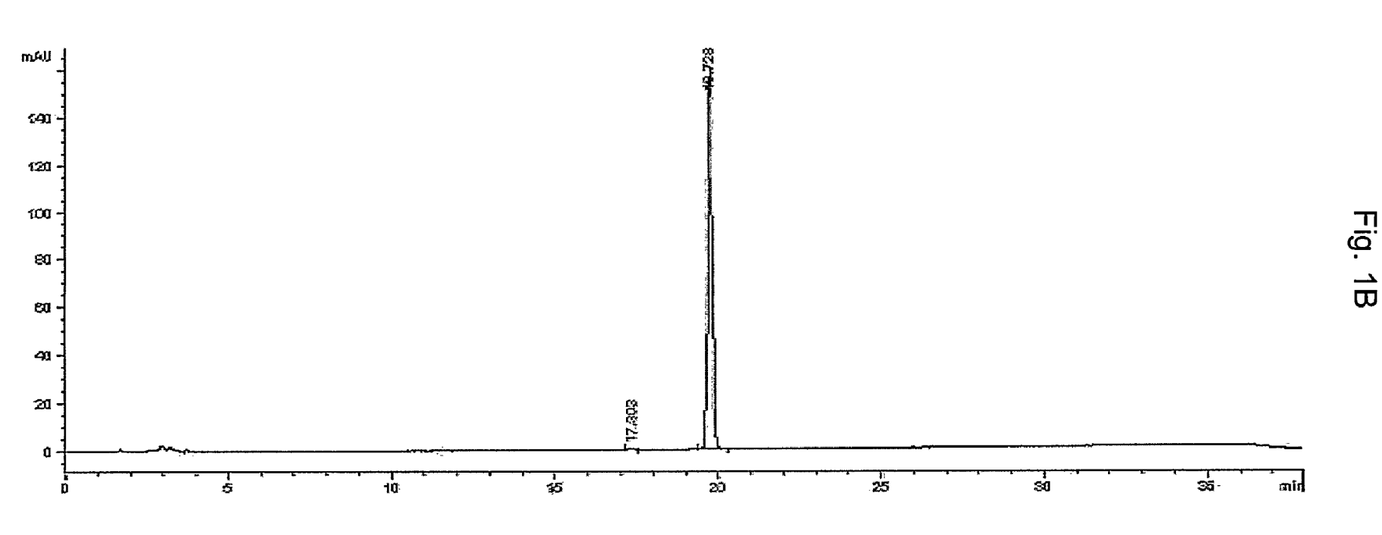
Figure 2A:
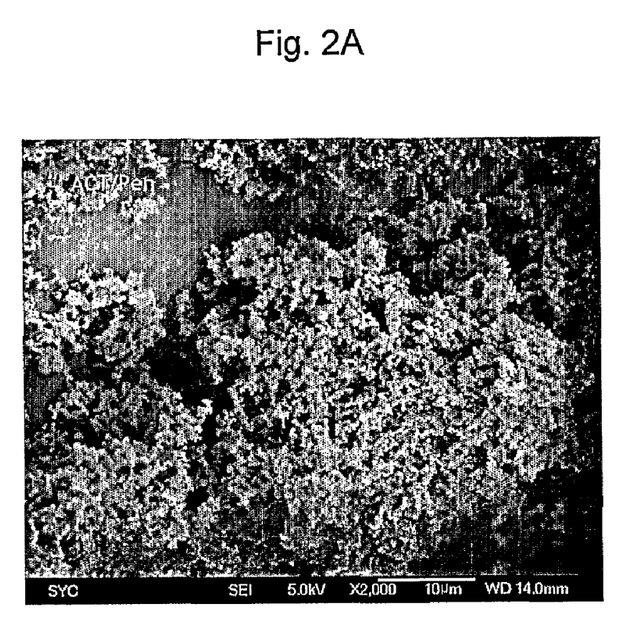
FIG. 2A shows SEM (Scanning Electron Microscopy) analysis results of amorphous docetaxel prepared by solvent precipitation of Example 1.
Figure 2B:
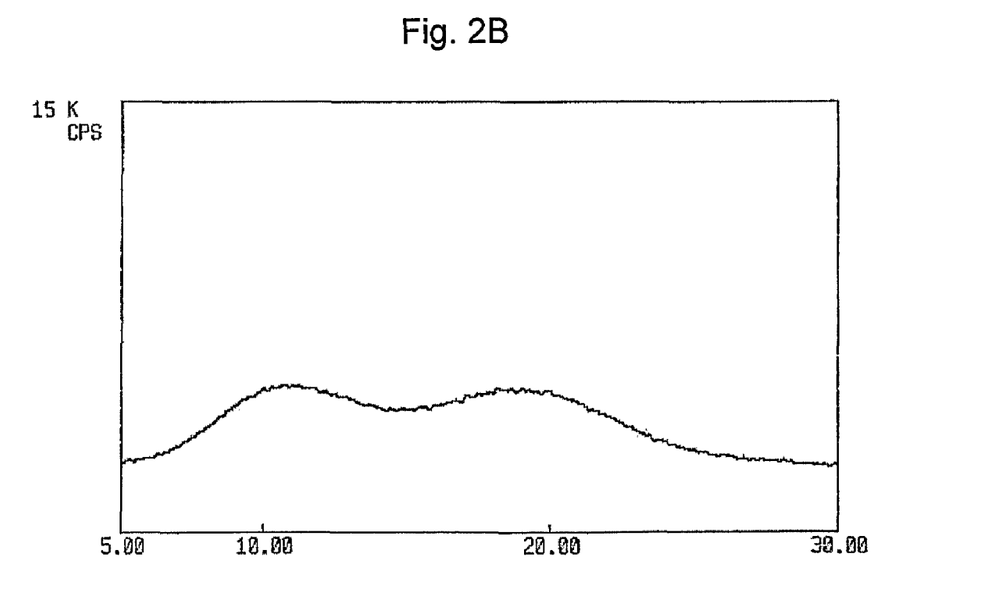
FIG. 2B shows XRPD (X-ray powder diffractometer) analysis results of the above-identified amorphous docetaxel.
Figure 3A:
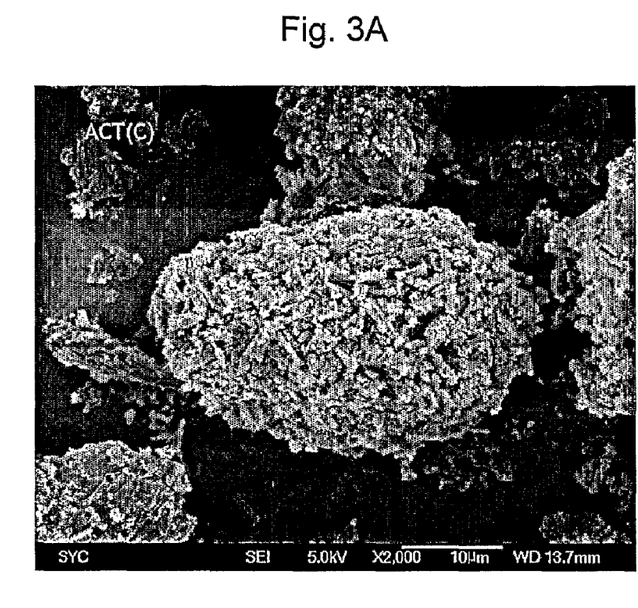
FIG. 3A shows SEM analysis results of anhydrous crystalline docetaxel prepared by colloid formation of Example 4.
Figure 3B:
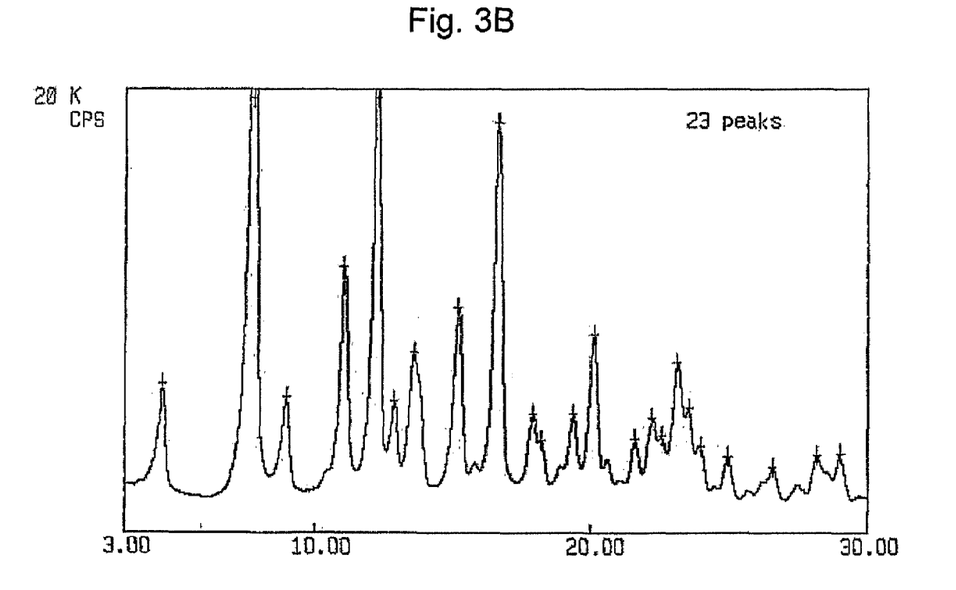
FIG. 3B shows XRPD analysis results of the above-identified anhydrous crystalline docetaxel.
Figure 4:
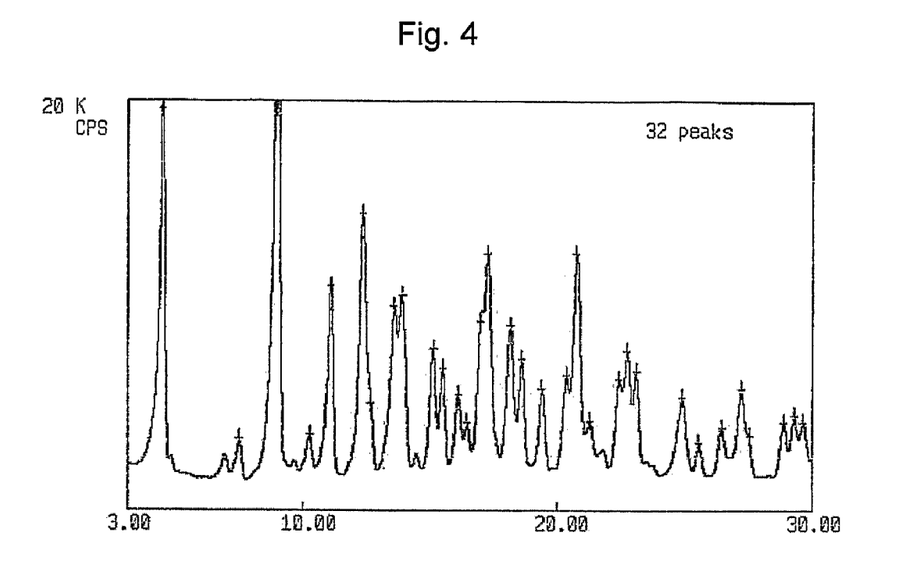
FIG. 4 shows XRPD analysis results of hydrated crystalline docetaxel prepared by solvent precipitation at a low temperature of Example 5.
Figure 5:
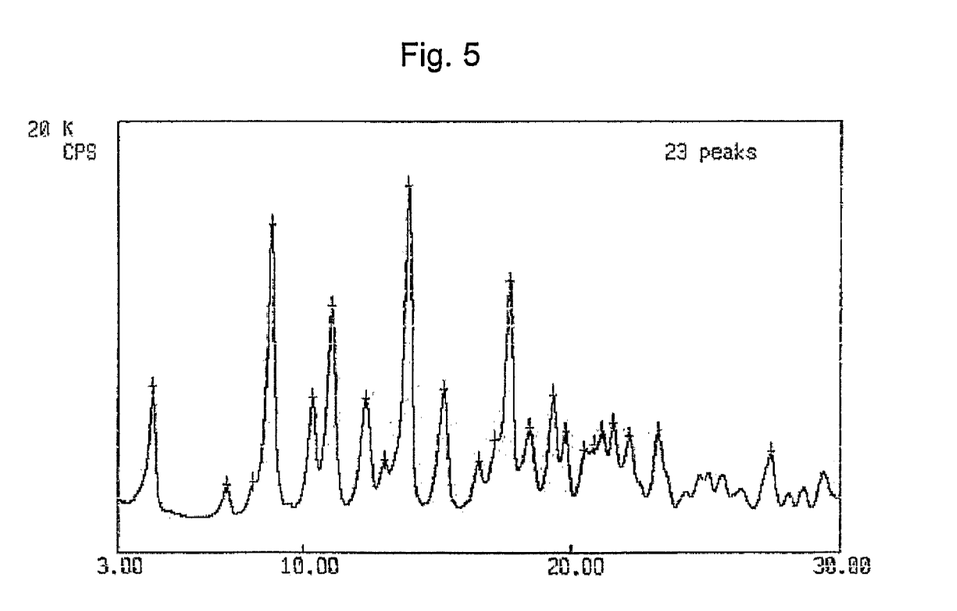
FIG. 5 shows XRPD analysis results of hydrated crystalline docetaxel prepared by reduced pressure evaporation after dissolution in a mixed solvent of an organic solvent and purified water of Example 6.
Figure 6:
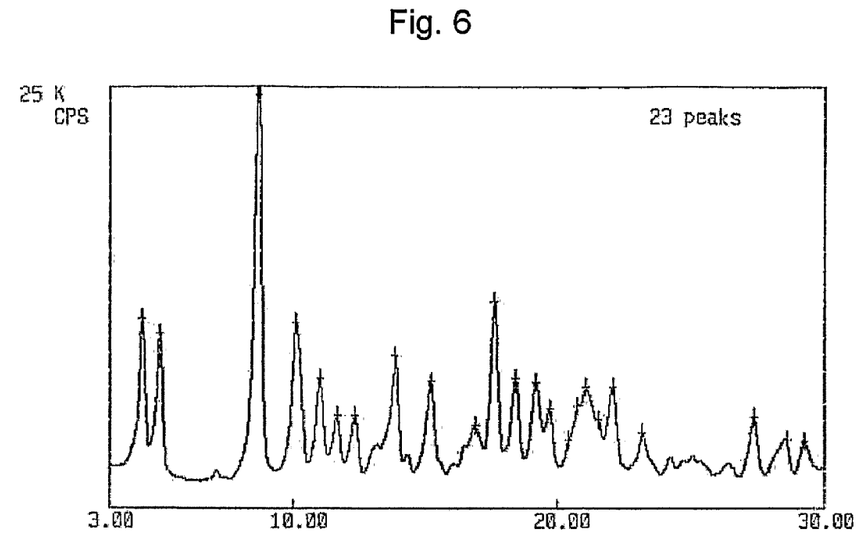
FIG. 6 shows XRPD analysis results of hydrated crystalline docetaxel prepared by the formation of precipitates by addition of purified water after dissolution in a mixed solvent of an organic solvent and purified water of Example 7.
Figure 7A:
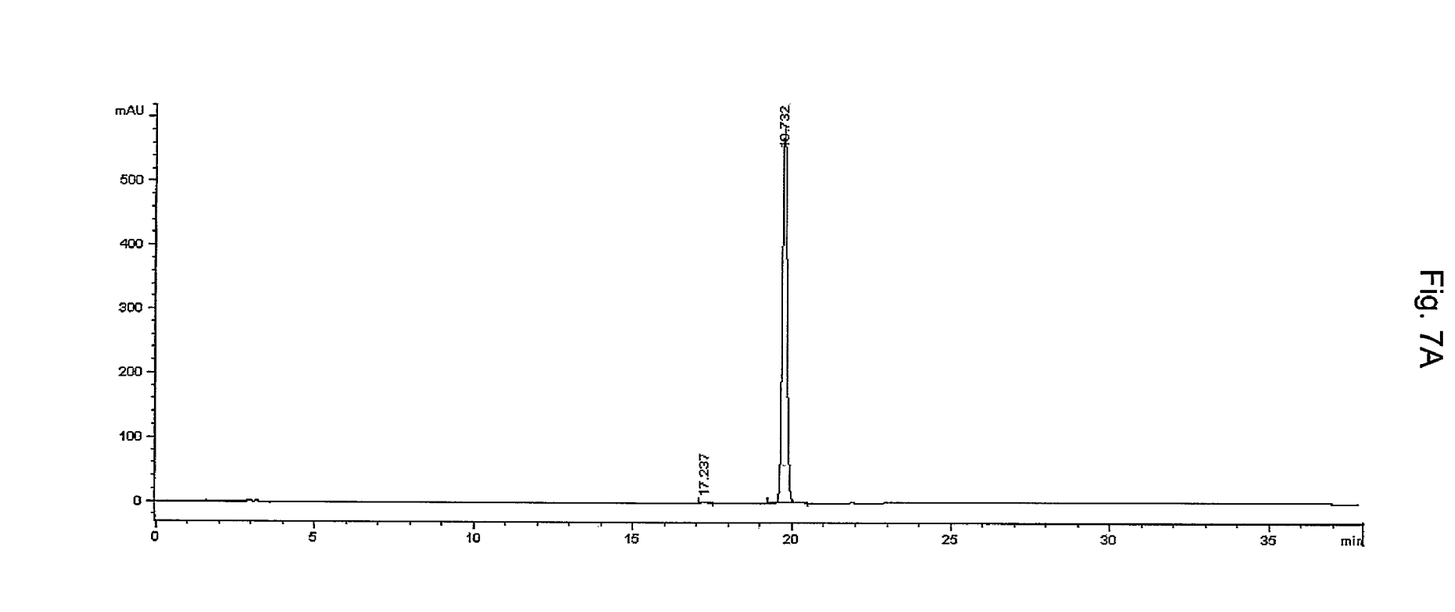
FIG. 7A shows HPLC analysis results of specimen before the preparation process.
Figure 7B:
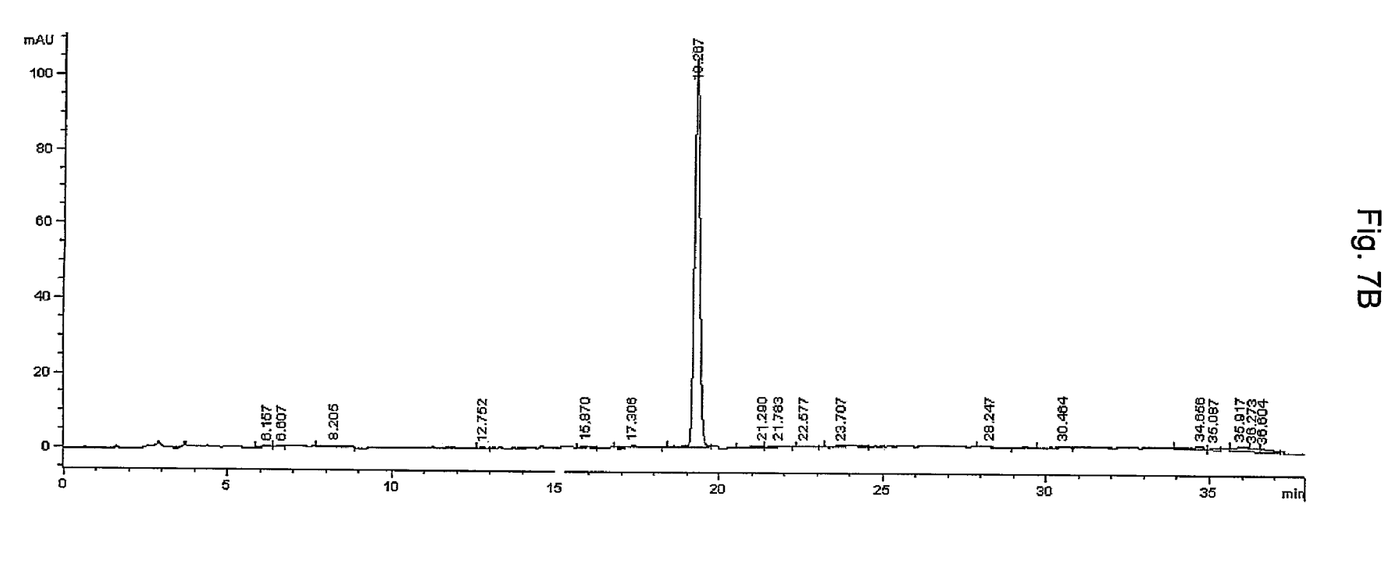
FIG. 7B shows HPLC results of the specimen after the preparation process.
Figure 7C:
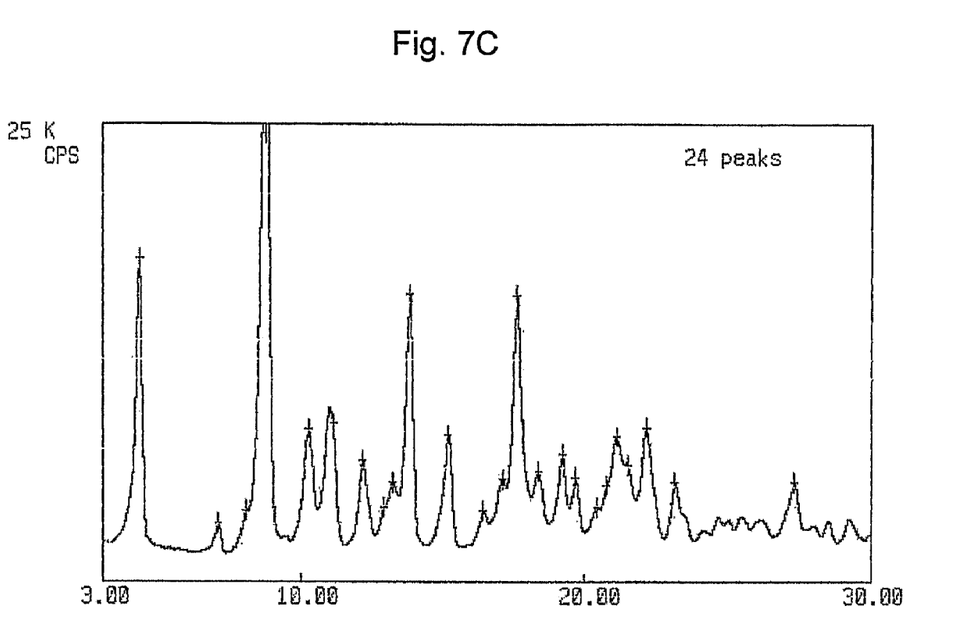

All specimens used were docetaxel having a purity of not less than 99.7% (FIG. 1A), and there was no purity decrease after the preparation process (FIG. 2B). After 2 g of docetaxel having a purity of 99.7% was dissolved in 20 ml of acetone at room temperature, the obtained solution was added to 200 ml of n-pentane while being stirred to thereby form a precipitate. After the obtained precipitate was filtered, vacuum drying was carried out at temperature of 40° C., at a vacuum degree of 650 mmHg for 15 hours to thereby obtain 1.94 g of amorphous docetaxel having a purity of 99.7%.

EXAMPLE 2

Preparation of Amorphous Docetaxel 2

After 2 g of docetaxel having a purity of 99.7% was dissolved in 20 ml of dichloromethane, it was added to 200 ml of n-pentane while being stirred to thereby instantly cause precipitation, and then the obtained precipitate was filtered and vacuum drying was carried out at a temperature of 40° C. and at a vacuum degree of 650 mmHg for 15 hours to thereby obtain 1.95 g of amorphous docetaxel having a purity of 99.7%.

EXAMPLE 3

Preparation of Amorphous Docetaxel 3

After 2 g of docetaxel having a purity of 99.7% was dissolved in 20 ml of dichloromethane, it was added to 200 ml of n-hexane while being stirred to thereby instantly cause precipitation, and then the obtained precipitate was filtered and vacuum drying was carried out at a temperature of 40° C. and at a vacuum degree of 650 mmHg for 15 hours to thereby obtain 1.92 g of amorphous docetaxel having a purity of 99.7%.

EXAMPLE 4

Preparation of Anhydrous Crystalline Docetaxel

After 2 g of docetaxel having a purity of 99.7% was dissolved in 10 ml of acetone, it was concentrated under a reduced pressure. 2 ml of acetone was again added to the obtained solution to thereby form a colloid where docetaxel was being suspended, not being completely dissolved. The solvent was evaporated from the obtained colloid at 35° C. to 40° C. using a Rotary evaporator, and vacuum drying was carried out at temperature of 40° C. and at vacuum degree of 650 mmHg for 15 hours to thereby obtain 1.96 g of anhydrous crystalline docetaxel having a purity of 99.7%.

EXAMPLE 5

Preparation of Hydrated Crystalline Docetaxel 1

After 250 mg of docetaxel having a purity of 99.7% was dissolved in 3 ml of methanol at room temperature and 3 ml of distilled water was slowly added thereto, it was allowed to stand at 4° C. for 24 hours for crystallization. The obtained crystal was filtrated and drying was carried out at temperature of 35° C., at vacuum degree of 650 mmHg for 15 hours thereby to obtain 254 mg of hydrated crystalline docetaxel having a purity of 99.7% (moisture: 4.5%).

EXAMPLE 6

Preparation of Hydrated Crystalline Docetaxel 2

300 mg of docetaxel having a purity of 99.7% was dissolved in 60 ml of a mixed solvent of acetone and distilled water having a mixing ratio of 7:3 by volume. The solvent among the obtained solution was evaporated at 35° C. to 40° C. using a Rotary evaporator. As the solvent evaporated, a precipitate was produced. The produced precipitate was filtrated and vacuum drying was carried out at a temperature of 35° C. and at a vacuum degree of 650 mmHg for 15 hours to thereby obtain 303 mg of hydrated crystalline docetaxel having a purity of 99.7% (moisture: 4.3%).

EXAMPLE 7

Preparation of Hydrated Crystalline Docetaxel by Dissolution in a Mixed Solvent of an Organic Solvent and Purified Water and Formation of Precipitate by Addition of Purified Water 300 mg of docetaxel having a purity of 99.7% was dissolved in 60 ml of a mixed solvent of methanol and distilled water having a mixing ratio of 8:2 by volume at room temperature. The obtained solution was slowly added to 300 ml of purified water to thereby form a precipitate. The obtained precipitate was filtrated and vacuum drying was carried out at temperature of 35° C. and at a vacuum degree of 650 mmHg for 15 hours to thereby obtain 311 mg of hydrated crystalline docetaxel having a purity of 99.7% (moisture: 4.6%).

COMPARATIVE EXAMPLE 1

In accordance with the method described in U.S. Pat. No. 6,838,569 by Arun Prakash Sharma et al, after 203 mg of docetaxel having a purity of 99.5% was dissolved in 6.11 ml of acetonitrile at a temperature of 68° C., 18.34 ml of purified water was slowly drop-wise added thereto while being stirred and stirring was then carried out at a temperature of 20° C. for 3 hours to thereby form a precipitate. The obtained precipitate was filtrated and vacuum drying was carried out at a temperature of 36° C. and at a vacuum degree of 650 mmHg for 36 hours to thereby obtain 162 mg of hydrated crystalline docetaxel having a purity of 78.8%.

It was verified that the conditions proposed in this comparative example were very unstable conditions where docetaxel could be degraded, although there could be variation in extent depending on applied temperatures and time periods.

COMPARATIVE EXAMPLE 2

To evaluate the stability of docetaxel in the case that hydrated crystalline docetaxel is prepared by dissolution in alcohols at a high temperature, methanol and ethanol were each used as an organic solvent and dissolution temperature and standing temperature were 50° C., and change in purity of docetaxel and degradation degree were measured after letting it stand for 0, 1, 5, 10, and 24 hours. The results are shown in Table 3 below. The measurement was carried out under the same HPLC conditions as shown in Table 2.

TABLE 3

| | MeOH | | EtOH | |
|---|---|---|---|---|
| | Change in Purity of Docetaxel (%) | 7-epi-docetaxel Amounts Produced (area %) | Change in Purity of Docetaxel (%) | 7-epi-docetaxel Amounts Produced (area %) |
| 0 hr | 99.7469 | 0 | 99.7480 | 0 |
| 1 hr | 95.7399 | 4.0163 | 99.2959 | 0.4494 |
| 5 hr | 81.8743 | 17.2282 | 97.8546 | 1.8948 |
| 10 hr | 69.3707 | 28.4728 | 96.8045 | 2.9451 |
| 24 hr | 50.7338 | 41.5352 | 95.1952 | 4.5544 |

As can be seen in Table 3, in the case of dissolution and standing at 50° C., most docetaxel was converted into its metabolite, 7-epi-docetaxel, and as time elapsed, the purity of docetaxel was remarkably decreased. This test shows that the temperature condition is very important for maintenance of purity and stability of docetaxel.

As described in the above, the present invention provides a method for selectively preparing amorphous, anhydrous crystalline, or hydrated crystalline docetaxel using several solvents. In accordance with the invention, amorphous, anhydrous crystalline, and hydrated crystalline docetaxel according to desired use can be selectively produced with a high yield while maintaining its initial high purity.

What is claimed is:

1. A method for the preparation of amorphous docetaxel, comprising:
    dissolving a docetaxel-containing matter or docetaxel in a polar solvent at a concentration of 1 to 30% (w/v);
    adding the above-obtained solution to a non-polar solvent of 5 times or higher thereof by volume to cause precipitation; and
    filtrating and drying the produced precipitate to obtain amorphous docetaxel, wherein the polar solvent is at least one selected from the group consisting of dichloromethane, chloroform and acetone, and the non-polar solvent is at least one selected from the group consisting of hexane, pentane, cyclohexane, cyclopentane and dialkylether.

2. A method for the preparation of anhydrous crystalline docetaxel, comprising:
    mixing 1 to 30% (w/v) of a docetaxel-containing matter or docetaxel and acetone and colloidizing it in a suspended state; and
    evaporating the acetone among the obtained colloid solution at 35° C. to 40° C. and drying it under a reduced pressure to obtain anhydrous crystalline docetaxel of fine powders.

3. A method for the preparation of hydrated crystalline docetaxel, comprising:
    dissolving a docetaxel-containing matter of docetaxel in a mixed solvent of an organic solvent and purified water having a mixing ratio of 7:0.5 to 7:5 by volume or a mixed solvent of an organic solvent and a buffer solution having a mixing ratio of 7:0.5 to 7:5 by volume at a concentration of 0.1 to 5% (w/v);
    producing a precipitate by evaporating the obtained solution at 35° C. to 40° C., thereby eliminating the organic solvent among the mixed solvent; and
    filtrating the obtained precipitate at a reduced pressure and drying it to prepare hydrated crystalline docetaxel, wherein the organic solvent is at least one selected from the group consisting of methanol, ethanol, propanol, acetone and acetonitrile, and the hydrated crystalline docetaxel is dihydrate.

* * * * *